United States Patent [19]
Rossiter

[11] Patent Number: 5,888,961
[45] Date of Patent: Mar. 30, 1999

[54] 1,3-DIOXANE AND ITS USE IN PERFUMERY

[75] Inventor: Karen Jane Rossiter, Ashford, Great Britain

[73] Assignee: Quest International B.V., Naarden, Netherlands

[21] Appl. No.: 913,810
[22] PCT Filed: Mar. 4, 1996
[86] PCT No.: PCT/EP96/00930
  § 371 Date: Dec. 10, 1997
  § 102(e) Date: Dec. 10, 1997
[87] PCT Pub. No.: WO96/30359
  PCT Pub. Date: Oct. 3, 1996

[30] Foreign Application Priority Data

Mar. 25, 1995  [EP]  European Pat. Off. ........... 95104442.9

[51] Int. Cl.$^6$ ...................................................... A61K 7/46
[52] U.S. Cl. ............................................. 512/12; 549/364
[58] Field of Search ................................ 549/369; 512/12

[56] References Cited

U.S. PATENT DOCUMENTS 3,423,430  1/1969  Cahn et al. ................................. 512/8

FOREIGN PATENT DOCUMENTS 039 029    11/1981  European Pat. Off. .
2 235 940  1/1975   France .
2 252 814  6/1975   France .
2 368 271  5/1978   France .

*Primary Examiner*—James H. Reamer
*Attorney, Agent, or Firm*—Pillsbury Madison & Sutro

[57] ABSTRACT

The invention provides the novel cyclic acetal 2-isobutyl-5-methyl-1,3-dioxane. This compound has attractive fragrance characteristics, i.e. a strong chamomile and fruity odor with aniseed, minty, camphor and green notes. The compound finds application as a fragrance material in a wide range of perfumes and perfumed products.

10 Claims, 1 Drawing Sheet isovaleraldehyde     2-methylpropane-1,3-diol     2-isobutyl-5-methyl-1,3-dioxane

1,3-DIOXANE AND ITS USE IN PERFUMERY

This application is the national phase of international application PCT/EP96/00930, filed Mar. 4. 1996 which designated the U.S.

FIELD OF THE INVENTION

This invention concerns a novel 1,3-dioxane and its use in perfumes and perfumed products.

BACKGROUND OF THE INVENTION

Various 1,3-dioxanes, also designated as cyclic acetals derived from an aldehyde and a 1,3-diol, are known in the perfumery literature.

Thus, in U.S. Pat. No. 4,146,506 perfume compositions comprising a 4-isopropyl-5,5-dimethyldioxane with an C1–C3 alkyl substituent in the 2 position have been described. The 1,3-dioxanes are said to have odour notes ranging from fruity, herbal to woody.

In EP 0 039 029 2-(1'-methylbutyl)-1,3-dioxanes are described which are substituted in the 4 and 5 position with at least 2 and in many cases 3 alkyl groups with a maximum total number of carbon atoms of 6. The compounds are said to have floral and fruity odour notes.

In NL-A-7305487 2-n.butyl-4,4,6-trimethyl-1,3-dioxane is described as having lavender, minty and laurel leaf odour notes. Also described therein are various other 4,4,6-trimethyl-1,3-dioxanes, some of which from S. Arctander, Perfume and Flavor Chemicals, Montclair, N.J., 1969, others from own evaluation. The judgement of their suitability for perfumery is mixed.

In NL-A-7305488 various 2-substituted 4-propyl-5-ethyl-1,3-dioxanes are described, again with mixed opinion as to their suitability for perfumery.

In NL-A-7415594 various 2,4 substituted 1,3-dioxanes (erroneously described as 2,6 substituted) are described, in particular 2-(4'-methylpent(en)yl)-4-methyldioxanes, as having woody, floral and fruity (citrussy) odour notes.

In DE-A-2334378 2-(2'-methyl-1'-propenyl)-1,3-dioxanes with one or more methyl or ethyl groups in the positions 4 and/or 5 and/or 6 are described as having a rose-like odour reminiscent to rose oxide.

Finally, in GB 981,285 various substituted 1,3-dioxanes are described in which the 2 position must be substituted with a C4–C9 alkyl group and the 4 position with a methyl group. These substitution requirement are stressed as importand for obtaining the desired geranium-rose odour.

SUMMARY OF THE INVENTION

The present invention provides the cyclic acetal 2-isobutyl-5-methyl-1,3-dioxane as well as perfume compositions and perfumed products comprising this compound in olfactively effective amounts.

DETAILED DESCRIPTION OF THE INVENTION

The novel acetal of the invention has attractive odour qualities, which may be described as a strong chamomile and fruity odour with anisseed, minty, camphor and green notes. This is unexpected, particularly in view of the rose-oxide like odour of the compounds described in DE-A-2334378

The dioxane according to the invention is a powerful fragrance material which may be used as such to impart, strengthen or improve the odour of a wide variety of products, or it may be used as a component of a perfume to contribute its odour character to the overall odour of such perfume. For the purposes of this invention a perfume is intended to mean a mixture of fragrance materials, if desired mixed with or dissoved in a suitable solvent or mixed with a solid substrate, which is used to impart a desired odour to the skin and/or any product for which an agreeable odour is indispensible or desirable. Examples of such products are: fabric washing powders, washing liquids, fabric softeners and other fabric care products; detergents and household cleaning, scouring and disinfection products; air fresheners, room sprays and pomanders; soaps, bath and shower gels, shampoos, hair conditioners and other personal cleansing products; cosmetics such as creams, ointments, toilet waters, preshave, aftershave, skin and other lotions, talcum powders, body deodorants and antiperspirants, etc.

Other fragrance materials which can be advantageously combined with the dioxane according to the invention in a perfume are, for example, natural products such as extracts, essential oils, absolutes, resinoids, resins, concretes etc., but also synthetic materials such as hydrocarbons, alcohols, aldehydes, ketones, ethers, acids, esters, acetals, ketals, nitriles, etc., including saturated and unsaturated compounds, aliphatic, carbocyclic and heterocyclic compounds.

Such fragrance materials are mentioned, for example, in S. Arctander, Perfume and Flavor Chemicals (Montclair, N.J., 1969), in S. Arctander, Perfume and Flavor Materials of Natural Origin (Elizabeth, N.J., 1960) and in "Flavor and Fragrance Materials—1991", Allured Publishing Co. Wheaton, Ill. USA.

Examples of fragrance materials which can be used in combination with the dioxane according to the invention are: geraniol, geranyl acetate, linalol, linalyl acetate, tetrahydrolinalol, citronellol, citronellyl acetate, dihydromyrcenol, dihydromyrcenyl acetate, tetrahydromyrcenol, terpineol, terpinyl acetate, nopol, nopyl acetate, 2-phenylethanol, 2-phenylethyl acetate, benzyl alcohol, benzyl acetate, benzyl salicylate, styrallyl acetate, benzyl benzoate, amyl salicylate, dimethylbenzylcarbinol, trichloromethylphenylcarbinyl acetate, p-tert-butylcyclohexyl acetate, isononyl acetate, vetiveryl acetate, vetiverol, α-hexylcinnamaldehyde, 2-methyl-3-(p-tert-butylphenyl)propanal, 2-methyl-3-(p-isopropyl-phenyl) propanal, 3-(p-tert-butylphenyl)-propanal, 2,4-dimethylcyclohex-3-enyl-carboxaldehyde, tricyclodecenyl acetate, tricyclodecenyl propionate, 4-(4-hydroxy-4-methylpentyl)-3-cyclohexenecarboxaldehyde, 4-(4-methyl-3- pentenyl)-3-cyclohexenecarboxaldehyde, 4-acetoxy-3-pentyltetrahydropyran, 3-carboxymethyl-2-pentylcyclopentane, 2-n-heptylcyclopentanone, 3-methyl-2-pentyl-2-cyclopentenone, n-decanal, n-dodecanal, 9-decenol-1, phenoxyethyl isobutyrate, phenyl-acetaldehyde dimethyl-acetal, phenylacetaldehyde diethylacetal, geranyl nitrile, citronellyl nitrile, cedryl acetate, 3-isocamphyl-cyclohexanol, cedryl methyl ether, isolongifolanone, aubepine nitrile, aubepine, heliotropin, coumarin, eugenol, vanillin, diphenyl oxide, hydroxycitronellal, ionones, methylionones, isomethylionones, irones, cis-3-hexenol and esters thereof, indan musks tetralin musks isochroman musks macrocyclic ketones, macrolactone musks, ethylene brassylate.

Solvents which can be used for perfumes which contain the dioxane according to the invention are, for example: ethanol, isopropanol, diethyleneglycol monoethyl ether, dipropylene glycol, diethyl phthalate, triethyl citrate, isopropyl myristate, etc.

The quantities in which the dioxane according to the invention can be used in perfumes or in products to be perfumed may vary within wide limits and depend, inter alia, on the nature of the product, on the nature and the quantity of the other components of the perfume in which the compound is used and on the olfactive effect desired. It is therefore only possible to specify wide limits, which, however, provide sufficient information for the specialist in the art to be able to use the ether-nitriles according to the invention for his specific purpose. In perfumes an amount of 0.01% by weight or more of the dioxane according to the invention will generally have a clearly perceptible olfactive effect. Preferably the amount is at least 0.1% by weight, more preferably at least 1%. The amount of the dioxane according to the invention present in products will generally be at least 10 ppm by weight, preferably at least 100 ppm, more preferably at least 1000 ppm. However, levels of up to about 20% by weight may be used in particular cases, depending on the product to be perfumed.

The dioxane occurs in both cis and trans isomers, and also exists as enantiomers of both isomers, and the invention covers all forms and also mixtures thereof.

The dioxane of the invention is easily accesible and is conveniently prepared by acid catalysed condensation of isovaleraldehyde with 2-methylpropane-1,3-diol in a generally conventional reaction. This is typically found to produce an isomer mix of betweeet 20% and 40% cis and between 80% and 60% trans. The mixture may be separated in its isomers by methods known in the art. However, for its use in perfumery this is not required.

BRIEF DESCRIPTION OF THE DRAWINGS

The invention will be further described, by way of illustration, in the following Examples and with reference to the accompanying drawings in which.

EXAMPLE 1

Figure 1:
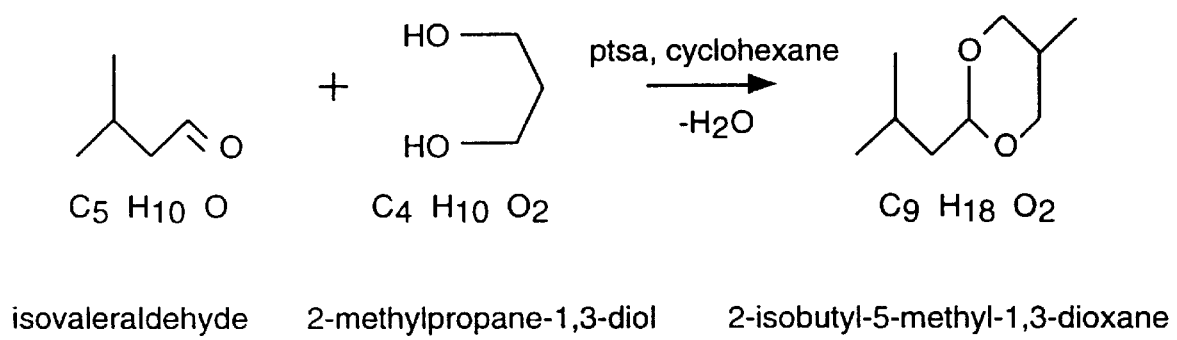
FIG. 1 shows the reaction scheme for preparation of the dioxane of the invention.

2-isobutyl-5-methyl-1,3-dioxane was prepared on a laboratory scale by acid catalysed condensation of isovaleraldehyde and 2-methylpropane-1,3-diol using a 1 litre 3 necked flask equipped with a Dean and Stark condenser, a thermometer and a mechanical stirrer. The reaction scheme is shown in FIG. 1.

Isovaleraldehyde (170 ml, 135.9 g, 1.58 mol), 2-methylpropane-1,3-diol (147 ml, 149.5 g, 1.74 mol) and p-toluenesulphonic acid monohydrate (2 g, 0.01 mol) were refluxed in cyclohexane (500 ml) with removal of water by the Dean and Stark condenser. After 6 hours the temperature of the reaction mixture had risen from 80° C. to 91° C. and 28.4 ml (exactly the theoretical amount) of water had been collected.

After cooling to room temperature, the reaction mixture was washed with a saturated solution of sodium carbonate (500 ml) and the solvent (along with traces of water from the wash) removed under vacuum on a rotary evaporator.

The residue (300 g) was distilled using a vigreux column (2.5 cm×30 cm) under reduced pressure and the fraction boiling in the range 82°–85° C. at 31 mbar collected. The yield was 200 g, 80%. The mass of residue was 32 g. The remaining mass was made up of recovered solvent.

EXAMPLE 2

A Herbal fantasy perfume for use at 0.2% w/w in all purpose cleaners was prepared according to the following recipe:

|  | % w/w |
|---|---|
| Para-tertbutyl-cyclohexanone | 0.7 |
| Pine American | 8.0 |
| Dihydromyrcenol (Q) | 8.0 |
| Eucalyptus Globulus | 1.3 |
| Dihydromyrcenyl acetate (Q) | 3.3 |
| Geraniol | 8.0 |
| Phenyl-ethyl alcohol | 8.0 |
| Bourgeonal (Q) | 2.7 |
| Hexyl-cinnamic aldehyde | 16.0 |
| Peppermint American Far West | 0.3 |
| Rose Oil Bulgarian | 0.7 |
| Florosa (Q) | 0.7 |
| Lavender Russian | 0.7 |
| Linalyl acetate | 35.0 |
| Product obtained according to Example 1 | 3.3 |
| Diethyl Phthalate | 3.3 |
|  | 100 |

(Q) > fragrance materials marketed by Quest International, Ashford, Kent, United Kingdom

I claim:
1. 2-isobutyl-5-methyl-1,3-dioxane.
2. The dioxane of claim 1, in the form of the cis isomer and/or the trans isomer.
3. The dioxane of claim 2, comprising a mixture of cis and trans isomers.
4. The dioxane of claim 3, comprising 20% to 40% cis isomer and 80% to 60% trans isomer.
5. The dioxane of claim 1, prepared by acid catalysed condensation of isovaleraldehyde with 2-methylpropane-1, 3-diol.
6. A perfume comprising the dioxane of claim 1 in an olfactively effective amount.
7. A perfume according to claim 6, wherein the dioxane is present in an amount of at least 0.01% by weight.
8. A perfume according to claim 7, wherein the dioxane is present in an amount of at least 0.1% by weight.
9. A perfumed product comprising the dioxane according to any one of claims 1–5.
10. A perfumed product comprising a perfume according to any one of claims 6–8.

* * * * *